United States Patent [19]

Sharrow

[11] Patent Number: 4,737,145

[45] Date of Patent: Apr. 12, 1988

[54] GUIDE FLUTES FOR CATHETER MANIFOLD

[75] Inventor: James S. Sharrow, St. Louis Park, Minn.

[73] Assignee: GV Medical, Inc., Minneapolis, Minn.

[21] Appl. No.: 916,238

[22] Filed: Oct. 7, 1986

[51] Int. Cl.⁴ ............................................. A61M 25/00
[52] U.S. Cl. ........................................ 604/83; 604/53
[58] Field of Search ................... 604/33, 83, 280, 283, 604/284, 82, 84, 85, 89, 236, 249, 258, 164, 169

[56] References Cited

U.S. PATENT DOCUMENTS 4,585,435  4/1986  Vaillancourt ......................... 604/83
4,655,746  4/1987  Daniels et al. ...................... 604/164

FOREIGN PATENT DOCUMENTS 041  12/1978  Japan .................................. 604/164

Primary Examiner—Richard C. Pinkham
Assistant Examiner—T. Brown
Attorney, Agent, or Firm—Orrin M. Haugen; Thomas J. Nikolai; Frederick W. Niebuhr

[57] ABSTRACT

A catheter manifold for an angioplasty balloon catheter assembly houses a plurality of serially arranged luers. Longitudinal sections of the luers are joined by tubular connectors, and with the connectors form a central passage through the manifold. At the most distal tubular connector is a reduction in passage diameter. A plurality of elongate, longitudinally directed flutes are formed in that connector just proximal of the diameter reduction. The flutes are engaged by a guide wire insertion tube or fiber insertion tube as it is loaded into the manifold, and tend to center the tube in the passageway. The flutes tend to maintain it in coaxial relation to the passageway, while permitting fluids from the proximal luers to flow in the passageway exteriorly of the tube.

7 Claims, 3 Drawing Sheets

GUIDE FLUTES FOR CATHETER MANIFOLD

BACKGROUND OF THE INVENTION

The present invention relates to laser enhanced transluminal angioplasty catheters and particularly to apparatus in such catheters for controllng the insertion of an optical fiber or guide wire into the catheter, and for facilitating the introduction of fluids into the catheter.

Angioplasty catheter devices have been found useful in treating occlusions formed in blood vessels, for example from plaque build-up. In a laser enhanced catheter, an optical fiber is used to transmit a beam of laser energy from a generator to the fiber distal end, where the laser energy is delivered to and against the obstruction. Also, medication is delivered to the treatment area through one or more lumens in the catheter. Under controlled medication and exposure to the laser energy, the obstruction is partially removed, reduced in size, or eliminated entirely, effectively re-opening the blood vessel to restore normal circulation.

One known device for this technique is constructed by joining the proximal end of the catheter to a catheter manifold comprised of a plurality of luers. Such a catheter assembly is described in U.S. Pat. No. 4,669,465 (Moore et al), assigned to the assignee of the present application. The forward or distal luer is used to control inflation of a balloon at the catheter tip, while treatment fluids can be supplied to the catheter lumen through the remaining, proximal luers. The use of two or more proximal luers enables simultaneous introduction of a plurality of treatment fluids, and in controlled proportions.

Typically, the catheter is inserted into a blood vessel requiring treatment by use of a guide wire loaded into the manifold by a guide wire insertion tube, then extended distally of the tube, through the manifold and into the catheter. The insertion tube prevents the guide wire from mistakenly entering one of the luers rather than the catheter lumen, and is withdrawn along with the guide wire once catheter insertion is complete.

The central passage through the catheter manifold must be large enough to accept the guide wire tube, and to allow fluids from the proximal luers to flow around the tube. At the same time, the diameter of the passage, at some point before the distal luer, must be reduced to the approximate size of the catheter lumen. This can hinder retrograde passage (withdrawal) of the guide wire, as the guide wire tube can drift out of its concentric relation within the central passage and become caught against the distal tip of the insertion tube. In some cases, this movement completely prevents removal of the guide wire from the catheter manifold, rendering the catheter assembly inoperative. Similar difficulties are encountered in a laser enhanced transluminal catheter when attempting to insert the optical fiber in the catheter and manifold.

It therefore is an object of the present invention to provide a means for capturing the distal end of a filament insertion tube when loaded into a catheter manifold, and further guiding it into a coaxial relation with the manifold central passage.

Another object of the invention is to provide a means for positively maintaining a filament insertion tube coaxial with the central passageway so long as it remains loaded in the catheter manifold.

Another object of the invention is to maintain a guide wire introducer tube coaxial with a catheter lumen to facilitate the feeding of a catheter over the exposed end of a guide or exchange wire and into a blood vessel, and further to facilitate the withdrawal of the guide wire from the distal catheter lumen into the guide wire introducer and out of the manifold, all without inadvertently entering a luer or puncturing the hemostasis seal.

A further object of the invention is to allow fluid flow around a guide wire introducer when fully inserted.

Another object is to align an introducer for guide wire insertion through the seal and past the luers.

Another object is to align the filament insertion tube for fiber advance simultaneous with flow of fluids through the catheter.

Yet another object of the present invention is to guide and maintain a filament insertion tube in a coaxial relation within the central passage of a catheter manifold, while permitting flow of fluids through the passage and about the tube exterior.

SUMMARY OF THE INVENTION

To achieve these and other objects, there is provided a multiple luer catheter assembly. The assembly includes a catheter manifold, and a catheter connector at its proximal end to the manifold. A plurality of luers are serially arranged in the manifold, each luer having a tubular longitudinal section contained in the manifold, and a tubular intake section for effecting fluid communication between its associated longitudinal section and the environment outside of the manifold. A plurality of tubular connector members are provided, each member positioned between and substantially coaxially joined with two adjacent longitudinal sections. The connectors and longitudinal sections form a passage enclosure defining a longitudinal passage through at least a portion of the manifold, and in fluid communication with a lumen of the catheter. A proximal portion of the passage has a nominal diameter, and a distal portion of the passage has a reduced diameter substantially less than the nominal diameter. An elongate guide means is formed in the passage enclosure along at least part of the proximal portion, and extends radially inward to form in the passage a coaxial guide conduit with an effective diameter substantially less than the nominal diameter. The guide means engages a tube loaded into the passage and permits fluid flow between the enclosure and tube exterior.

Preferably, the passage diameter reduction from the nominal to reduced diameter is located in the most distal connector member, with the guide means also located in that connector member. The guide means can include a plurality of elongate, longitudinally directed flutes, with their proximal ends inclined distally and radially inward. Also, the catheter assembly can include a substantially rigid filament insertion tube and a filement contained in the tube and extensible distally into the catheter lumen when the tube is loaded into the passage. The guide means permits fluid flow in the passage outside of the tube when loaded in the passage.

The tube diameter can be substantially equal to the effective diameter, and preferably is slightly larger, with the flutes constructed of a plastic material. Then, as the tube is inserted into the manifold, its distal end is initially captured, then guided to a centered, coaxial relation with the passage as it is further inserted. Upon complete insertion, the flutes tend to maintain the tube in its coaxial relation, and also frictionally maintains it within the catheter manifold.

Between the longitudinal flutes is a substantially annular channel in the passageway exteriorly of the insertion tube. Fluids from the proximal luers readily flow through this channel to the distal portion of the passageway. Thus, the flutes ensure proper loading of the filament insertion tube or guide wire introducer, maintain its coaxial relation, and assist in securing it in the catheter manifold, all without interfering with flow of fluids to the catheter.

IN THE DRAWINGS

These and other features and advantages of the invention are more clearly understood upon reading the following detailed description and consideration of the accompanying drawings, in which.

Figure 5:
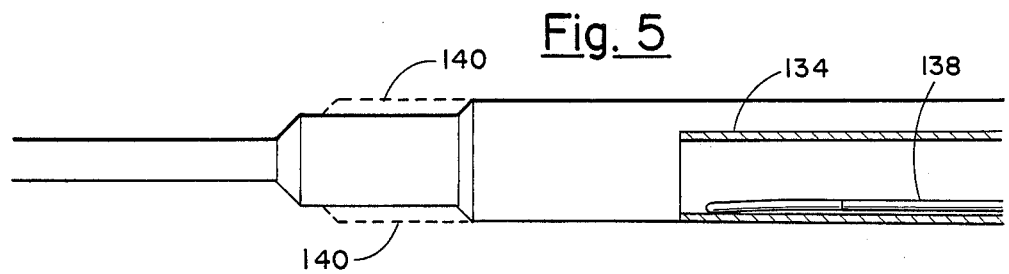
Figure 6:
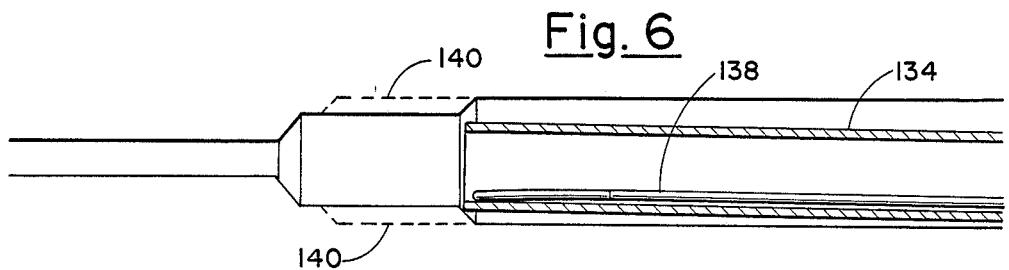
Figure 7:
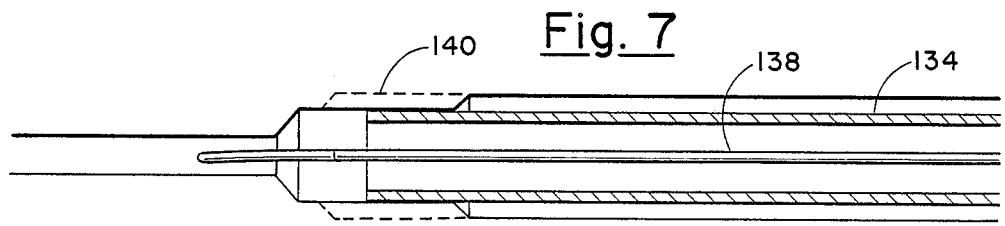

FIGS. 5–7 schematically illustrate the insertion of a filament guide tube into the catheter manifold.

DETAILED DESCRIPTION OF THE PREFERRED EMBODIMENT

Figure 1:
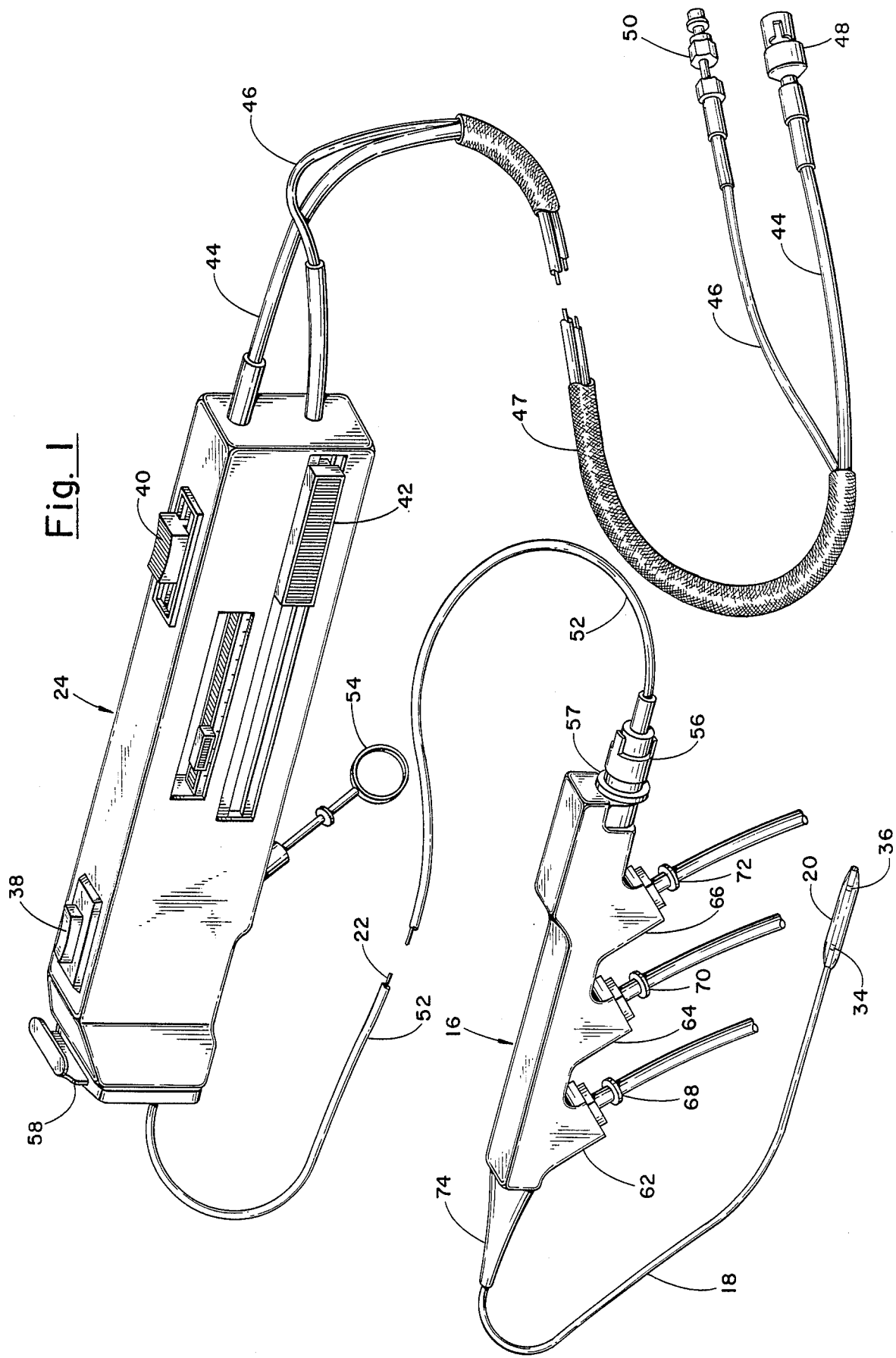
FIG. 1 is a perspective view of a fiber advance housing and catheter manifold constructed in accordance with the present invention.

Turning now to the drawings, there is shown in FIG. 1 an angioplasty catheter assembly including a catheter manifold 16 and an angioplasty catheter 18 extended from the forward or distal end of the catheter manifold. At the distal end of the catheter is a balloon 20. The laser enhancement fiber assembly including the fiber advancing housing 24, the cables 47 and optical fiber sheath 52, is a discrete device, separate from the balloon catheter assembly.

When attached to the catheter and in the fully advanced condition, an optical fiber 22 is contained in catheter 18, and runs rearwardly from the catheter through the catheter manifold into a fiber advance housing 24, whereby the optical fiber may be advanced or retracted in the catheter. If desired, radiopaque markers are provided near the catheter distal end as shown at 34 and 36, to enable a physician to determine the location of the catheter when it is inserted into a vessel.

As seen in the figure, fiber advance housing 24 and catheter manifold 16 are separable from one another, which enables a controlled insertion of optical fiber 22 through the manifold and into catheter 18. Provided on the top of housing 24 is a laser actuator switch 38, electrically connected to a power supply and laser source, for enabling the transmission of laser energy through optical fiber 22. Rearwardly of switch 38 is zero adjust slide 40, which comprises a movable member mounted to slide longitudinally with respect to the housing. Also movable slidably in the housing is a fiber advance member 42.

Extended from the rearward end of fiber advance housing 24 is an electrical cable 44 through which laser actuator switch 38 and zero adjust slide 40 are electrically linked to the laser control system. Adjacent cable 44 is an optical fiber cable 46 which contains a portion of optical fiber 22. A flexible sleeve 47 keeps the cables together. An electrical connector 48 at the proximal end of electric cable 44 is adapted for connection to the laser control system, while an optical connector 50 at the proximal end of the optical fiber cable optically links fiber 22 with the laser source.

Between fiber advance housing 24 and catheter manifold 16 is an optical fiber sheath 52 which enters the forward end of the fiber advance housing and emerges beneath the housing to a pull ring 54. The sheath is connected to a sheath connector 56 shown against a manifold connector 57 at the rearward end of manifold 16. The fiber advance housing, sheath, and cables 44 and 46 are a discrete assembly separate from the manifold and catheter. However, a housing connector latch 58, mounted on the forward end of the fiber advance housing, lockingly engages manifold connector 57 to connect the fiber advance housing to catheter manifold 16 when desired. A fiber insertion tube (not shown), integral with sheath connector 56, extends longitudinally into manifold 16.

The catheter manifold has first, second and third extensions 62, 64 and 66, to which are connected first, second and third luers 68, 70 and 72. First luer 68 provides fluids to balloon 20 in order to control its inflation and deflation. Second and third luers 70 and 72 deliver treatment fluids, as required, to a central lumen in catheter 18. A conical relief member 74 supports the proximal portion of catheter 18 near the manifold forward end, protecting it against sharp bends.

Figure 2:
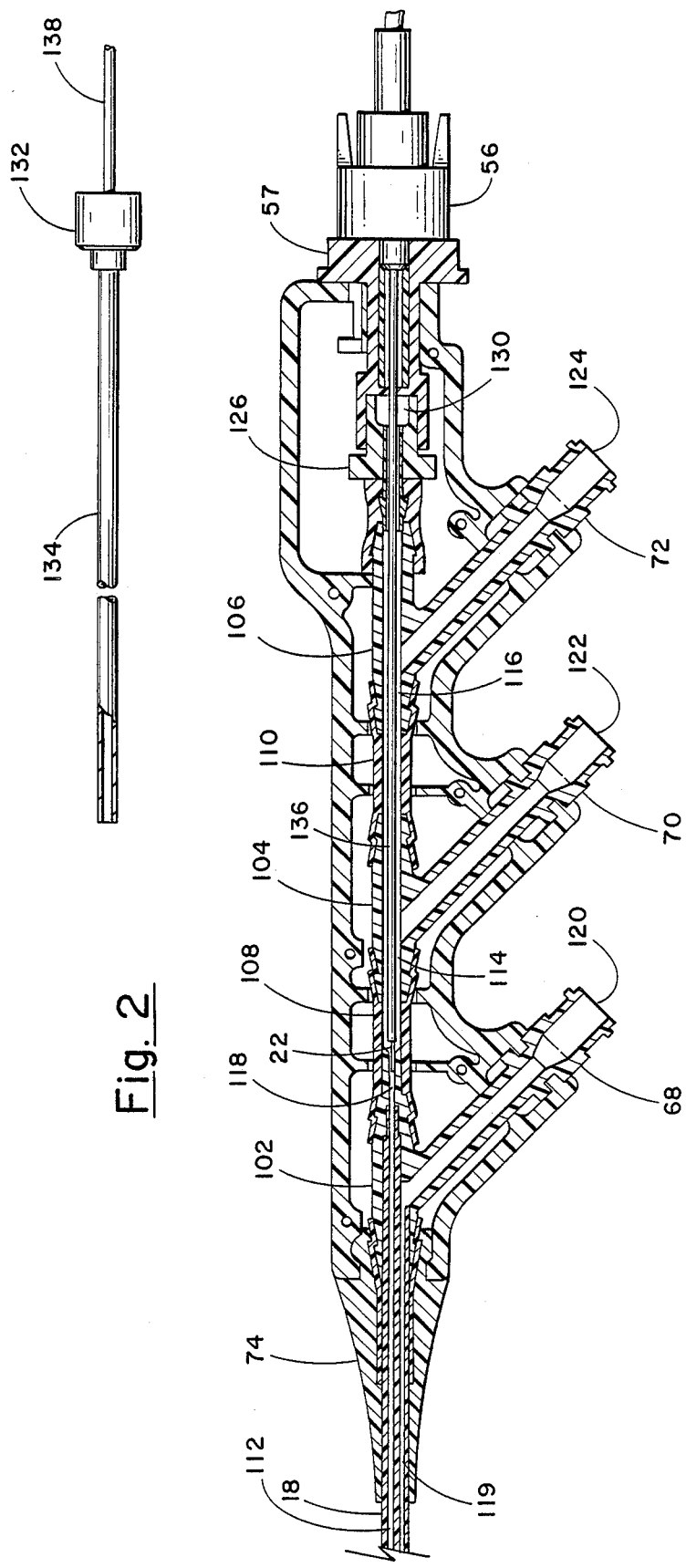
FIG. 2 is a sectional side elevation of the catheter manifold of FIG. 1.

In FIG. 2 it is seen that first, second and third luers 68, 70 and 72 have upper longitudinal sections or luer branch fittings 102, 104 and 106, respectively, joined together by first and second tubular connectors 108 and 110 of a heat shrink tubing. Formed through first section 102 is a central longitudinal bore having a diameter corresponding to that of a central lumen 112 in catheter 18. Larger longitudinal bores are provided through second and third upper sections 104 and 106. Thus, the longitudinal sections and tubular connectors form in catheter manifold 16 an enclosure defining a single central passage 114 with a proximal or rearward portion 116 of a nominal diameter, and a reduced diameter distal portion 118, with the diameter reduction occurring along first connector 108. A first central bore 120 of first luer 68 is open to a balloon inflation lumen 119 (FIG. 3), while second and third central bores 122 and 124 of luers 70 and 72, respectively, are open to enlarged portion 116 and reduced catheter lumen 112. A seal retaining cap 126 and manifold connector 57 enclose a seal 130, which prevents backflow of fluids introduced into the passageway through the luers.

Shown next to manifold 16, and insertable into manifold 16, through an opening in its proximal end, is a guide wire assembly including a guide connector 132, a forwardly extended guide wire insertion tube 134 integral with the guide connector. A guide wire 138 is inserted into and past the connector 132 and the insertion tube 134. With the guide wire insertion tube assembly fully loaded into the manifold, guide connector 132 lies face-to-face against manifold connector 57, and the distal end of guide wire insertion tube 134 is positioned near the distal end of proximal portion 116. This is the same configuration as that shown for the fully inserted optical fiber assembly, with sheath connector 56 against the manifold connector and a fiber insertion tube 136 extended into virtually the entire length of the proximal portion. With the guide wire assembly loaded into manifold 16, guide wire 138 is advanced relative to the rest of the guide wire assembly, into the distal portion of central passage 114 and then into lumen 112 of catheter 18.

Guide wire insertion tube 134 assists in directing guide wire 138 to distal portion 118 of the central passage, ensuring that the guide wire does not erroneously enter either of central bores 122 and 124 as it travels through the passage. Insertion tube 134 further must substantially center the guide wire in the central passage, particularly to enable its direct travel into the reduced diameter distal portion of the central passage. Accurate centering and guidance is particularly critical in that guide wire 138 typically has a coiled and slightly bent distal end.

Figure 3:
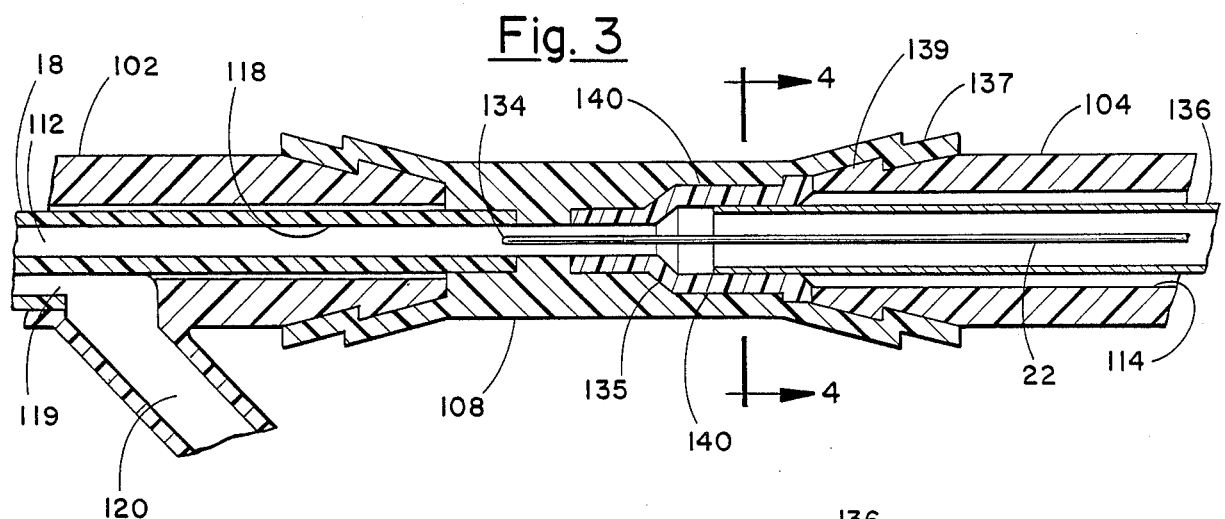
FIG. 3 is an enlarged view of a portion of FIG. 2.

FIG. 2 shows that sheath connector 56 and its integral fiber insertion tube 136 are similar in structure to the guide wire connector and insertion tube, and facilitate insertion of optical fiber 22 through the manifold into catheter 18 in much the same manner as described in connection with the guide wire. Hence, another requirement for tube 136 as seen from FIG. 3 is that its outside diameter must be sufficiently small, in relation to the nominal diameter of proximal portion 116, to enable flows of fluids through the central passage along the tube exterior and into distal portion 118. The ability to permit fluid flow is particularly important during use of the catheter assembly, when the guide wire assembly has been withdrawn from manifold 16 and replaced by the sheath connector and fiber insertion tube. FIG. 3 also illustrates opposed notched ends 137 and 139 of connector 108 and section 104, respectively. Similar ends of the remaining connectors and sections ensure their interlocking coaxial engagement.

Figure 4:
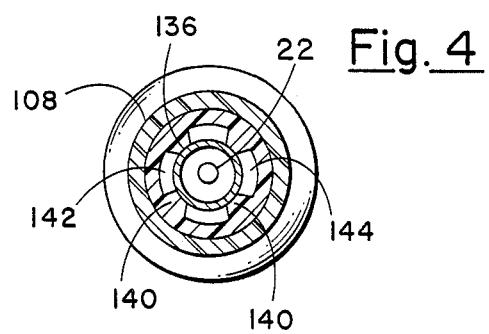
FIG. 4 is a sectional view taken along the line 4—4 in FIG. 3.

FIGS. 3 and 4 show a guide means formed in first connector 108 for maintaining a filament insertion tube, such as guide wire tube 134 or fiber tube 136, in a coaxial relation with passage 114, both to ensure proper entry of a guide wire, optical fiber or other filament into distal passage portion 118, and to facilitate passage of the guide wire from the distal to the proximal end of the catheter. The guide means includes an insert or tubular guide member 135 having four elongate, longitudinally directed and symmetrically arranged flutes 140. The flutes are formed symmetrically in guide member 135, with the guide member in turn mounted principally in that part of first tubular connector 108 having the nominal diameter. The flutes extend radially inward to form a coaxial guide conduit with an effective diameter substantially less than the nominal diameter.

Guide member 135 is constructed of a plastic material, and flutes 140 are formed as radially inward extensions of the member. Preferably the effective conduit diameter is equal to the exterior diameter of fiber insertion tube 36 (or guide wire insertion tube 134). Then, when the tube is fully loaded into the manifold, it contacts all four flutes as shown in FIG. 4. Flutes 140 cooperate to ensure proper centering of tube 136 and further frictionally engage the tube, to more securely retain the tube in manifold 16. Fluid flow through central passage 16 in the area of flutes 140 occurs through four arcuate sectors 142, which together form a generally annular fluid channel 144 in passage 114.

In FIG. 3 it is seen that guide member 135 is formed to provide proximal faces of flutes 140 which incline radially inward and distally. This is to ensure that the flutes capture the distal end of a filament insertion tube as it is inserted into catheter manifold 16, and then guide the tube distal end toward its coaxial relation to passageway 114 responsive to further loading. FIGS. 5-7 schematically illustrate the sequence of such loading, in this case loading of guide wire insertion tube 134. During the initial loading stage, the distal end of guide wire insertion tube 134 tends to ride along one of the edges of central passage 114, and thus is not coaxial with the central passage. The proximal faces of flutes 140, however, provide a ramp surface which directs the tube distal end toward its centered position as the tube is further inserted, as shown in FIG. 6. Upon reaching the end of the proximal faces of the flutes, the distal end of tube 134 is properly centered, and is readily moved to the fully inserted location represented in FIG. 7. Fiber insertion tube 136, during its insertion, is centered in the same manner.

Catheter insertion into a blood vessel requiring treatment is accomplished with catheter manifold 16 separated from fiber advance housing 24. With the guide wire assembly fully loaded into manifold 16, guide wire 138 is inserted into and through the manifold, then together, catheter 18 and guide wire 138 are inserted into the vessel requiring treatment. Insertion tube 134 facilitates insertion of the guide wire as previously explained.

Alternately, catheter 18 can be inserted and advanced over the guide wire to the desired location within the vessel, and guide wire 138 is withdrawn. Because flutes 140 retain the distal end of insertion tube 134 in its coaxial relation to central passageway 114, retrograde passage (withdrawal) of the guide wire occurs without any binding against an offcenter insertion tube. Once guide wire 138 is withdrawn into tube 134, the entire guide wire assembly is withdrawn from manifold 16.

At this stage, a fiber insertion tube can be inserted into the manifold, bringing manifold connector 57 and sheath connector 56 in face-to-face relation, and locating the distal tip of the fiber insertion tube near to the distal end of proximal portion 116. Hence, the fiber insertion tube assists loading of optical fiber 22 in the same manner as guide wire insertion tube 134 facilitates loading of the guide wire.

Pull ring 54 then is used to draw sheath 52 rearwardly through the housing, in effect, to advance housing 24 along the sheath toward the catheter manifold, to simultaneously advance optical fiber 22 into and through catheter 18. By virtue of a lengthwise slit along the sheath, it is separated from the optical fiber inside the housing as it is moved rearwardly.

Once sheath 52 has been drawn backwardly a sufficient amount to bring the forward edge of housing 24 over manifold connector 57, connector latch 58 secures the manifold connector to integrally join the manifold and housing, and positioning the distal tip of optical fiber 22 just short of the distal tip of catheter 18. At this point, zero adjust slide 40 is moved longitudinally to establish a zero point, and the laser can be activated only when fiber advance member 42 is moved forwardly beyond this point. Retraction of fiber advance member 42 to the zero point automatically disables the laser.

During the angioplasty procedure, fluids administered through luers 70 and 72 readily flow to the catheter lumen through arcuate sectors 142. This permits a steady supply of fluids if desired, even during operation of the laser. Following the angioplasty procedure, the physician withdraws optical fiber 22. The fiber insertion tube is maintained in coaxial relation to central passage 114, and thus ensures trouble-free withdrawal of the optical fiber.

What is claimed is:

1. A multiple luer catheter assembly including:

a catheter manifold, and a catheter connected at its proximal end to the manifold;

a plurality of luers serially arranged in said manifold, each luer having a tubular longitudinal section contained in said manifold and a tubular intake section for enabling fluid communication between the associated longitudinal section and the environment outside of said manifold;

a plurality of tubular connector members, each connector member positioned between and substantially coaxially joined with two adjacent longitudinal sections, said connector members and longitudinal sections forming an enclosure defining a longitudinal passage through at least a portion of said manifold and in fluid communication with a lumen of said catheter, said passage having a proximal portion with a nominal diameter, and a distal portion with a reduced diameter substantially less than said nominal diameter; and an elongate guide means formed in said enclosure along at least part of said proximal portion and extended radially inward to form in said passage a coaxial guide conduit with an effective conduit diameter substantially less than said nominal diameter, said guide means engaging and capturing a distal end of a tube as said tube is removably loaded into said passage by a proximal end of the passage, to substantially align said tube distal end coaxially with said proximal portion while permiting fluid flow through said passage to said lumen between said enclosure and tube exterior.

2. The catheter assembly of claim 1 wherein:
said guide means are located near the distal end of said proximal portion of the passage.

3. The catheter assembly of claim 2 wherein:
the reduction in passage diameter from said nominal diameter to said reduced diameter, and said guide means, are located in the distal one of said connector members.

4. The apparatus of claim 3 wherein:
said guide means comprise a tubular guide member mounted in said distal connector member, and a plurality of elongate, longitudinally directed flutes formed in said guide member as radially inward extensions of said guide member.

5. The catheter assembly of claim 1 wherein:
said guide means comprise a plurality of elongate, longitudinally directed flutes extending radially inwardly of said enclosure along said proximal portion.

6. The catheter assembly of claim 5 wherein:
said flutes, at their proximal ends, are inclined distally and radially inward.

7. The catheter assembly of claim 6 wherein:
said tube comprises a substantially rigid filament insertion tube containing a filament extensible distally into said lumen when the tube is fully loaded into said passage, said tube having an exterior diameter substantially equal to said effective conduit diameter.

* * * * *